US012788858B2

(12) United States Patent
Ravindranath et al.

(10) Patent No.: US 12,788,858 B2
(45) Date of Patent: Nov. 10, 2026

(54) DIALYSIS SYSTEM HAVING EXTERNAL TUBING SURFACE CLEANING

(71) Applicants: BAXTER INTERNATIONAL INC., Deerfield, IL (US); BAXTER HEALTHCARE SA, Glattpark (CH)

(72) Inventors: Aporva Raj Makam Ravindranath, Shivamogga (IN); Akhilesh Sham Sundar Vibhute, Gulbarga (IN); Sachin Sunkad, Bangalore (IN)

(73) Assignees: Vantive US Healthcare LLC, Deerfield, IL (US); Vantive Health GmbH, Glattpark (CH)

( * ) Notice: Subject to any disclaimer, the term of this patent is extended or adjusted under 35 U.S.C. 154(b) by 204 days.

(21) Appl. No.: 18/367,073

(22) Filed: Sep. 12, 2023

(65) Prior Publication Data

US 2024/0082470 A1 Mar. 14, 2024

(51) Int. Cl.

| | |
|---|---|
| ***B08B 1/20*** | (2024.01) |
| ***A61L 2/18*** | (2026.01) |
| ***A61L 2/26*** | (2006.01) |
| ***A61M 1/16*** | (2006.01) |
| ***A61M 1/28*** | (2006.01) |
| ***B08B 1/16*** | (2024.01) |
| *A61L 103/15* | (2026.01) |

(52) U.S. Cl.

CPC ............... *A61M 1/285* (2013.01); *A61L 2/18* (2013.01); *A61L 2/26* (2013.01); *A61M 1/169* (2013.01); *B08B 1/165* (2024.01); *B08B 1/20* (2024.01); *A61L 2103/15* (2026.01); *A61M 2209/10* (2013.01)

(58) Field of Classification Search

CPC .......... A61L 2/18; A61L 2/26; A61L 2202/24; B08B 1/165; B08B 1/20; A61M 1/169; A61M 1/285; A61M 2209/10

See application file for complete search history.

(56) References Cited

U.S. PATENT DOCUMENTS

| | | | | |
|---|---|---|---|---|
| 2007/0161946 A1* | 7/2007 | Cerasoli | ................ | A61M 39/18 604/29 |
| 2021/0244840 A1* | 8/2021 | Mermel | .................... | A61L 2/10 |
| 2022/0023005 A1 | 1/2022 | Chigbue et al. | | |
| 2022/0203005 A1* | 6/2022 | Jansson | ............... | A61M 1/1601 |

FOREIGN PATENT DOCUMENTS

| | | |
|---|---|---|
| CN | 111 760 105 | 10/2020 |

OTHER PUBLICATIONS

International Search Report—PCTUS2023/032477 dated Dec. 19, 2023—3 pages.
Written Opinion—PCTUS2023/032477 dated Dec. 19, 2023—3 pages.
IPRP—PCTUS2023/032477 dated Aug. 6, 2024—6 pages.

* cited by examiner

*Primary Examiner* — John Kim
(74) *Attorney, Agent, or Firm* — K&L Gates LLP

(57) ABSTRACT

A peritoneal dialysis ("PD") system includes a housing, a PD fluid pump housed by the housing, and a reusable line in fluid communication with the PD fluid pump. The reusable line is configured to be pulled into the housing. The PD system also includes an external tubing surface cleaning unit positioned and arranged to at least one of (i) remove debris from at least a portion of the exterior of the reusable line as it is pulled into the housing, or (ii) apply disinfectant to at least the portion of the exterior of the reusable line as it is pulled into the housing.

18 Claims, 6 Drawing Sheets

DIALYSIS SYSTEM HAVING EXTERNAL TUBING SURFACE CLEANING

PRIORITY CLAIM

This application claims priority to and the benefit of Indian Provisional Patent Application Ser. No. 202241052404, filed on Sep. 14, 2022, the entire disclosure of which is hereby incorporated by reference.

BACKGROUND

The present disclosure relates generally to medical fluid treatments and in particular to dialysis fluid treatments that require the pumping of patient-injectable fluids.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins, and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins, and excess water to take place. The source may include multiple liters of dialysis fluid including several solution bags.

The PD machines pump used or spent dialysate from the patient's peritoneal cavity, though the catheter, to a drain. As with the manual process, several drain, fill, and dwell cycles occur during dialysis. A "last fill" may occur at the end of an APD treatment. The last fill fluid may remain in the peritoneal chamber of the patient until the start of the next treatment, or may be manually emptied at some point during the day.

In any of the above modalities, the automated machine and even manual CAPD operate typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste and that does so in an aseptic manner.

SUMMARY

The present disclosure sets forth an automated peritoneal dialysis ("PD") system that provides improved reusability. The system includes a PD machine or cycler. The PD machine is capable of delivering fresh, heated PD fluid to the patient at, for example, 14 kPa (2.0 psig) or higher. The PD machine is capable of removing used PD fluid or effluent from the patient at, for example, between −5 kPa (−0.73 psig) and −15 kPa (−2.2 psig), such as −9 kPa (−1.3 psig) or higher. Fresh PD fluid may be delivered via a dual lumen patient line to the patient and is first heated to body fluid temperature, e.g., 37° C. The heated PD fluid is then pumped through a fresh PD fluid lumen of the dual lumen patient line to a disposable filter set, which is connected to the patient's transfer set, which is in turn connected to an indwelling catheter leading into the patient's peritoneal cavity. The disposable filter set communicates fluidly with the fresh and used PD fluid lumens of the dual lumen patient line. The disposable filter set is provided in one embodiment as a last chance filter for the PD machine, which may be heat disinfected between treatments.

The system may include one or more PD fluid container or bag that supplies fresh PD fluid to the PD machine or cycler. The PD machine or cycler may include internal lines having two-way or three-way valves and at least one PD fluid pump for pumping fresh PD fluid from the one or more PD fluid container or bag to a patient and for removing used PD fluid from the patient to a house drain or drain container. One or more flexible PD fluid line leads from the PD machine or cylcer's internal lines to the one or more PD fluid container or bag. The flexible dual lumen patient line mentioned above leads from the PD machine or cylcer's internal lines to the patient. A flexible drain line leads from the PD machine or cylcer's internal lines to the house drain or drain container. The system in one embodiment disinfects all internal lines, the PD fluid lines and the dual lumen patient line after treatment for reuse in the next treatment. The disinfection may involve heat disinfection using left-over fresh PD fluid.

The PD system in one embodiment retracts the reusable dual lumen patient line into a housing of the PD machine during disinfection. To do so, the PD machine may include an internal hose reel that pulls the dual lumen patient line into the housing. Maintaining the dual lumen patient line within the housing during disinfection is advantageous because the patient line is held in a coiled arrangement such that there is less surface area to lose heat. Also, the coiled patient line is retained within the housing, which acts as a thermal insulator relative to ambient temperature and ambient air fluctuations. In short, retracting the patient line into the housing during heat disinfection increases the efficiency of same.

A problem associated with retracting the dual lumen patient line into the housing is that debris collected by the patient line may be pulled into the housing. The debris may contaminate the internal components of the PD machine and possibly migrate into the inside of patient tubing. The PD machine and associated system and method of the present disclosure solves the debris collection problem by providing an external tubing surface cleaning unit that removes debris from the tubing and applies a disinfectant to the tubing as the tubing is pulled into the housing of the PD machine.

The external tubing surface cleaning unit in one embodiment includes a collar having an inner diameter that has a shape that matches an outer diameter shape of the dual lumen patient line. The dual lumen patient line may have a circular or substantially circular outer diameter in which case the collar includes a matching circular inner diameter. Alternatively, the dual lumen patient line may have an oblong or elliptical outer diameter in which case the collar includes a matching oblong or elliptical inner diameter. The inner diameter of the collar may be slightly larger than the outer diameter of the dual lumen patient line.

A foam scrubber is provided along the inner diameter of the collar, such that the foam scrubber extends around and contacts a full 360 degrees of the dual lumen patient line as the patient line is pulled through the external tubing surface cleaning unit of the present disclosure. The foam scrubber accordingly has a cylindrical or tubular portion that is held, e.g., mechanically press-fit and/or adhered, within the collar. The foam scrubber also includes a disinfectant application extension that extends from the cylindrical or tubular portion into a disinfectant reservoir. The disinfectant reservoir holds a disinfectant, such as an environmentally friendly disinfectant, e.g., citric acid or a povidone-iodine solution. The disinfectant application extension of the foam scrubber allows the disinfectant to flow or migrate from the disinfectant reservoir to the foam scrubber cylindrical or tubular portion, where the disinfectant may then be transferred to the exterior surface of the dual lumen patient line as it is pulled through the external tubing surface cleaning unit. The foam scrubber accordingly wipes off the external surface of the patient line and applies disinfectant to same.

The foam scrubber may be made for example from polyurethane flexible foam or silicone foam, e.g., with a shore hardness ranging from Shore A50 to Shore A60, which has good absorption properties when dipped with disinfectant, for example, a povidone-iodine solution or citric acid. The collar and the reservoir are made of plastic in one embodiment, such as, polyvinylchloride ("PVC") or a non-PVC material, such as polyethylene ("PE"), polyurethane ("PU"), polycarbonate ("PC") and/or poly etheretherketone ("PEElc").

The reservoir includes a sealed septum or other type of openable sealed closure that accepts a syringe or other type of disinfectant administration device. The patient or caregiver periodically fills the syringe or other disinfectant administration device with disinfectant, e.g., citric acid or a povidone-iodine solution. The patient then inserts a distal tip of the disinfectant administration device through the openable sealed closure and causes disinfectant to be distributed from the disinfectant administration device into the reservoir to fill the reservoir with disinfectant. Once the filling of the reservoir is complete, the user or caregiver removes the disinfectant administration device from the reservoir, after which the openable sealed closure either self-seals closed or is sealed closed via the patient or caregiver, e.g., applying a threaded cap.

Knowing when to refill the disinfectant reservoir may be accomplished in a plurality of ways. In one embodiment, the disinfectant level is visible to the user, wherein at least a portion of the reservoir is made of a clear or non-opaque material such that the patient or caregiver is able to visually discern when to add disinfectant to the reservoir. Alternatively or additionally, one or more low level sensor is provided with the PD machine. The low level sensor is positioned and arranged adjacent to the reservoir so as to be able to detect when the level of disinfectant has fallen below a refill level, indicating that the reservoir needs to be refilled. The sensor sends a signal to a control unit of the PD machine that is indicative of the low disinfectant level, upon which the control unit may cause a user interface of the PD machine to provide an audio, visual or audiovisual message to the patient or caregiver instructing that the disinfectant reservoir needs to be refilled. The one or more low level sensor may, for example, be a Hall Effect, magnetic, inductive, capacitive or optical sensor.

Alternatively or additionally, the control unit may cooperate with the patient or caregiver to know when to refill the reservoir with disinfectant. In one embodiment, the patient upon refilling the disinfectant reservoir presses or enters a refill confirm button or input into the control unit. The control unit at that point knows that the reservoir is full. The control unit is also programmed to know how much disinfectant is used for each retraction of the dual lumen patient line, i.e., how many disinfection sequence patient line retractions may be performed after the disinfectant reservoir is refilled. When the control unit determines that the current retraction is at or near the refill limit, the control unit causes the user interface of the PD machine to provide an audio, visual or audiovisual message to the patient or caregiver instructing that the disinfectant reservoir needs to be refilled.

The external tubing surface cleaning unit of the present disclosure may be implemented in a plurality of different ways. In a first way, the cleaning unit is provided primarily as an integrated and largely durable or reusable unit. The collar and reservoir are permanent unless damaged and needing replacement, while the foam scrubber may be a semi-permanent component that is replaced periodically. The patient is provided with a reusable syringe or other disinfectant administration device and a supply of disinfectant, such as citric acid or a povidone-iodine solution, which is replaced periodically. The external tubing surface cleaning unit is located within the housing of the PD machine, such that it is largely hidden from the patient or caregiver. The septum or other type of openable sealed closure provided at the reservoir is visible and accessible from outside the housing, such that the reservoir may be accessed by the patient or caregiver for disinfectant refill.

In a second way, the external tubing cleaning unit is provided as a detachable and replaceable unit. Here, the collar, reservoir and foam scrubber may be semi-permanent components, wherein the external tubing cleaning unit is removed and replaced as a whole when needed, e.g., when the foam scrubber needs replacement. The septum or other type of openable sealed closure may again be provided at the reservoir so that the patient or caregiver can introduce new disinfectant when needed. The patient is provided with a reusable syringe or other disinfectant administration device and a supply of disinfectant, such as citric acid or a povidone-iodine solution, which is replaced periodically. In an alternative embodiment, openable sealed closure is not provided and the external tubing cleaning unit is instead replaced when the reservoir runs out of disinfectant. In any embodiment, the reservoir of the detachable and replaceable unit may be provided with a tab or other feature sized and shaped to snap-fit into a mating aperture formed in the housing of the PD machine. A portion of the collar may also be used to snap-fit into a mating aperture formed in the housing of the PD machine. Providing multiple snap-fitting engagements helps the external tubing cleaning unit to remain stable while the reusable line, e.g., reusable dual lumen patient line is pulled through the cleaning unit while being scrubbed and disinfected via contact with the foam scrubber.

In light of the disclosure set forth herein, and without limiting the disclosure in any way, in a first aspect of the present disclosure, which may be combined with any other aspect, or portion thereof, a peritoneal dialysis ("PD") system includes a housing; a PD fluid pump housed by the housing; a reusable PD fluid line in fluid communication with the PD fluid pump, the reusable PD fluid line positioned and arranged to be pulled into the housing; and an external tubing surface cleaning unit configured and positioned to at least one of (i) remove debris from at least a portion of the exterior of the reusable PD fluid line as it is pulled into the housing or (ii) apply disinfectant to at least the portion of the exterior of the reusable PD fluid line as it is pulled into the housing.

In a second aspect of the present disclosure, which may be combined with any other aspect, or portion thereof, the reusable PD fluid line is a reusable patient line.

In a third aspect of the present disclosure, which may be combined with any other aspect, or portion thereof, the reusable patient line is a reusable dual lumen patient line.

In a fourth aspect of the present disclosure, which may be combined with any other aspect, or portion thereof, the PD system includes a hose reel located within the housing, the hose reel configured to pull the reusable PD fluid line into the housing.

In a fifth aspect of the present disclosure, which may be combined with any other aspect, or portion thereof, the PD system includes a control unit configured to cause a disinfection sequence to be performed in which an interior of the reusable PD fluid line is disinfected, and wherein the reusable PD fluid line is pulled into the housing prior to the disinfection sequence being performed.

In a sixth aspect of the present disclosure, which may be combined with any other aspect, or portion thereof, the external tubing surface cleaning unit includes a scrubber sized and shaped to extend around and contact the reusable PD fluid line to remove debris from at least the portion of the exterior of the reusable PD fluid line as it is pulled into the housing.

In a seventh aspect of the present disclosure, which may be combined with any other aspect, or portion thereof, the scrubber is a foam or fibrous scrubber formed so as to apply disinfectant to at least the portion of the exterior of the reusable PD fluid line as it is pulled into the housing.

In an eighth aspect of the present disclosure, which may be combined with any other aspect, or portion thereof, the foam or fibrous scrubber includes a cylindrical portion sized and shaped to extend around and apply disinfectant to the reusable PD fluid line, and a disinfectant application extension extending from the cylindrical portion into a disinfectant reservoir, wherein the disinfectant application extension allows disinfectant from the disinfectant reservoir to flow to the cylindrical portion.

In a ninth aspect of the present disclosure, which may be combined with any other aspect, or portion thereof, the cylindrical portion of the foam or fibrous scrubber is supported by a collar, the disinfectant reservoir extending from the collar.

In a tenth aspect of the present disclosure, which may be combined with any other aspect, or portion thereof, the external tubing surface cleaning unit includes a disinfectant reservoir configured to hold a disinfectant for application to at least the portion of the exterior of the reusable PD fluid line as it is pulled into the housing.

In an eleventh aspect of the present disclosure, which may be combined with any other aspect, or portion thereof, the disinfectant reservoir includes an openable sealed closure configured to allow disinfectant to be introduced into the reservoir.

In a twelfth aspect of the present disclosure, which may be combined with any other aspect, or portion thereof, the PD system includes a disinfectant administration device, wherein the openable sealed closure is configured to receive a tip of the disinfectant administration device such that the disinfectant administration device is able to introduce disinfectant into the reservoir.

In a thirteenth aspect of the present disclosure, which may be combined with any other aspect, or portion thereof, the PD system includes a source of disinfectant and a tube leading from the source of disinfectant to the reservoir.

In a fourteenth aspect of the present disclosure, which may be combined with any other aspect, or portion thereof, the external tubing surface cleaning unit is located within the housing.

In a fifteenth aspect of the present disclosure, which may be combined with any other aspect, or portion thereof, the housing provides an opening allowing an openable sealed closure of the external tubing surface cleaning unit to be accessed for refilling disinfectant.

In a sixteenth aspect of the present disclosure, which may be combined with any other aspect, or portion thereof, the external tubing surface cleaning unit is attachable to and detachable from the housing.

In a seventeenth aspect of the present disclosure, which may be combined with any other aspect, or portion thereof, the housing defines at least one mating aperture, and wherein the external tubing surface cleaning unit includes at least one feature sized and shaped to snap-fit within the at least one mating aperture.

In an eighteenth aspect of the present disclosure, which may be combined with any other aspect, or portion thereof, the external tubing surface cleaning unit includes a disinfectant reservoir, and wherein the system includes at least one sensor positioned and arranged to detect a level of disinfectant within the disinfectant reservoir.

In a nineteenth aspect of the present disclosure, which may be combined with any other aspect, or portion thereof, the PD system includes a control unit and a user interface, the at least one sensor outputting to the control unit, and wherein the control unit is configured to cause the user interface to prompt for a disinfectant refill when an output from the at least one sensor indicates a low disinfectant level within the disinfectant reservoir.

In a twentieth aspect of the present disclosure, which may be combined with any other aspect, or portion thereof, the PD system includes at least one ultraviolet ("UV") light positioned and arranged to disinfect the exterior of the reusable PD fluid line as it is pulled into the housing.

In a twenty-first aspect of the present disclosure, which may be combined with any other aspect, or portion thereof, the PD system includes a source of disinfectant and a tube leading from the source of disinfectant into the external tubing surface cleaning unit so as to be able to apply disinfectant to at least the portion of the exterior of the reusable PD fluid line as it is pulled into the housing.

In a twenty-second aspect of the present disclosure, which may be combined with any other aspect, or portion thereof, a peritoneal dialysis ("PD") system includes a PD machine including a housing; a reusable PD fluid line positioned and arranged to be pulled into the housing; and an external tubing surface cleaning unit configured and positioned to at least one of (i) remove debris from at least a portion of the exterior of the reusable PD fluid line as it is pulled into the housing or (ii) apply disinfectant to at least the portion of the exterior of the reusable PD fluid line as it is pulled into the housing.

In a twenty-third aspect of the present disclosure, which may be combined with any other aspect, or portion thereof, a peritoneal dialysis ("PD") method includes enabling a reusable PD fluid line to be retracted into a PD fluid machine; and causing at least one of (i) debris from at least a portion of the exterior of the reusable PD fluid line to be removed or (ii) disinfectant to be applied to at least the portion of the exterior of the reusable PD fluid line as it is retracted into the housing.

In a twenty-fourth aspect of the present disclosure, which may be combined with any other aspect, or portion thereof, any of the features, functionality and alternatives described in connection with any one or more of FIGS. 1 to 9 may be combined with any of the features, functionality and alternatives described in connection with any other of FIGS. 1 to 9.

In light of the above aspects and present disclosure set forth herein, it is an advantage of the present disclosure to provide a dialysis system and method that reduce disposable waste in an aseptic manner.

It is another advantage of the present disclosure to provide a dialysis system and method that help to prevent debris and other matter from entering a dialysis machine.

It is a further advantage of the present disclosure to provide a PD system that is easy to reload with a disinfectant.

It is yet another advantage of the present disclosure to provide a dialysis system and method that help to reduce service and replacement of a reusable tube.

It is a yet a further advantage of the present disclosure to provide a PD system and method that increase safety associated with reusable tubing.

Additional features and advantages are described in, and will be apparent from, the following Detailed Description and the Drawings. The features and advantages described herein are not all-inclusive and, in particular, many additional features and advantages will be apparent to one of ordinary skill in the art in view of the figures and description. Also, any particular embodiment does not have to have all of the improvements or advantages listed herein, and it is expressly contemplated to claim individual advantageous embodiments separately. In particular, the system of the present disclosure may have any one or more or all of the drip prevention structure and methodology, PD fluid container emptying structure and methodology and patient connection before drain check structure and methodology described herein. Moreover, it should be noted that the language used in the specification has been selected principally for readability and instructional purposes, and not to limit the scope of the inventive subject matter.

BRIEF DESCRIPTION OF THE FIGURES DRAWINGS

DETAILED DESCRIPTION

System Overview

Figure 1:
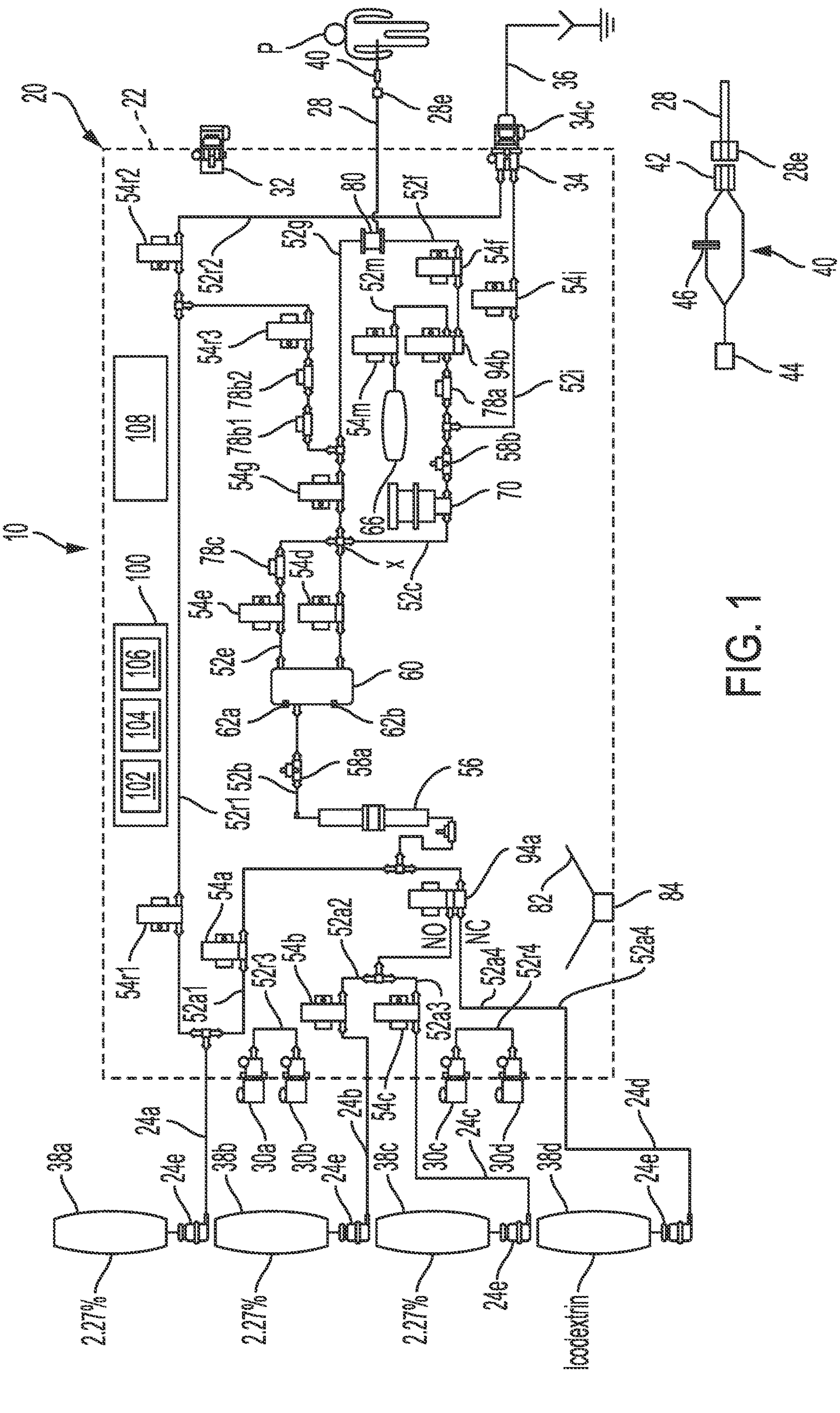
FIG. 1 is a fluid flow schematic of one embodiment for a medical fluid system, e.g., a PD fluid system, that is set for treatment.

Referring now to the drawings and in particular to FIG. 1, a medical system having the external tubing surface disinfection of the present disclosure is illustrated via peritoneal dialysis ("PD") system 10. System 10 includes a PD machine or cycler 20 and a control unit 100 having one or more processor 102, one or more memory 104, video controller 106 and user interface 108. User interface 108 may alternatively or additionally be a remote user interface, e.g., via a tablet or smartphone. Control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. Control unit 100 in an embodiment controls all electrical fluid flow and heating components of system 10 and receives outputs from all sensors of system 10. System 10 in the illustrated embodiment includes durable and reusable components that contact fresh and used PD fluid, which necessitates that PD machine or cycler 20 be disinfected between treatments, e.g., via heat disinfection.

System 10 in FIG. 1 includes an inline resistive heater 56, reusable supply lines or tubes **52*a*1 to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, PD fluid pump 70, temperature sensors 58*a* and 58*b*, pressure sensors 78*a*, 78*b*1, 78*b*2 and 78*c*, reusable patient tubing or lines 52*f* and 52*g* having respective valves 54*f* and 54*g*, reusable dual lumen patient line 28, a spring-actuated hose reel 80 for retracting patient line 28, reusable drain tubing or line 52*i* extending to drain line connector 34 and having a drain line valve 54*i*, and reusable recirculation tubing or lines 52*r*1 and 52*r*2 operating with respective disinfection valves 54*r*1 and 54*r*2. A third recirculation or disinfection tubing or line 52*r*3 extends between disinfection or PD fluid line connectors 30*a* and 30*b* for use during disinfection. A fourth recirculation or disinfection tubing or line 52*r*4 extends between disinfection connectors 30*c* and 30*d*** for use during disinfection.

System 10 further includes PD fluid containers or bags **38*a* to 38*c* (e.g., holding the same or different formulations of PD fluid), which connect to distal ends 24*e* of reusable PD fluid lines 24*a* to 24*c*, respectively. System 10*d* further includes a fourth PD fluid container or bag 38*d* that connects to a distal end 24*e* of reusable PD fluid line 24*d*. Fourth PD fluid container or bag 38*d* may hold the same or different type (e.g., icodextrin) of PD fluid than provided in PD fluid containers or bags 38*a* to 38*c*. Reusable PD fluid lines 24*a* to 24*d* extend in one embodiment through apertures (not illustrated) defined or provided by housing 22 of cycler 20**.

System 10 in the illustrated embodiment includes four disinfection or PD fluid line connectors **30*a* to 30*d* for connecting to distal ends 24*e* of reusable PD fluid lines 24*a* to 24*d*, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28*e* of reusable dual lumen patient line 28 into the other PD fluid lumen. Reusable supply tubing or lines 52*a*1 to 52*a*4 communicate with reusable supply lines 24*a* to 24*d*, respectively. Reusable supply tubing or lines 52*a*1 to 52*a*3 operate with valves 54*a* to 54*c*, respectively, to allow PD fluid from a desired PD fluid container or bag 38*a* to 38*c* to be pulled into cycler 20. Three-way valve 94*a* in the illustrated example allows for control unit 100 to select between (i) 2.27% (or other) glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 94*a***.

System 10 is constructed in one embodiment such that drain line **52*i* during a patient fill is fluidly connected downstream from PD fluid pump 70. In this manner, if drain valve 54*i* fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34*c* to form a closed disinfection loop. PD fluid pump 70** may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of cycler 20 and a corresponding leak detection sensor 84 outputting to control unit 100. In the illustrated example, system 10 is provided with an additional pressure sensor **78*c* located upstream of PD fluid pump 70, which allows for the measurement of the suction pressure of pump 70 to help control unit 100 more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c***.

System 10 in the example of FIG. 1 includes redundant pressure sensors **78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along a line including a third recirculation valve 54*r*3. System 10 may further employ one or more cross, marked via an X in FIG. 1**, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 94*b* via a citric acid valve 54*m* located along a citric acid line 52*m*. Citric acid line 52*m* is connected in one embodiment to the normally closed port of second three-way valve 94*b*, so as to provide redundant valves between disinfectant container or bag 66 and the PD fluid circuit during treatment. The redundant valves ensure that no citric acid reaches the treatment fluid lines during treatment. Citric acid is used instead during disinfection.

Control unit 100 in an embodiment uses feedback from any one or more of pressure sensors 78*a* to 78*c* to enable PD machine 20 to deliver fresh, heated PD fluid to the patient at, for example, 14 kPa (2.0 psig) or higher. The pressure feedback is used to enable PD machine 20 to remove used PD fluid or effluent from the patient at, for example, between −5 kPa (−0.73 psig) and −15 kPa (−2.2 psig), such as −9 kPa (−1.3 psig) or higher (more negative). The pressure feedback may be used in a proportional, integral, derivative ("PID") pressure routine for pumping fresh and used PD fluid at a desired positive or negative pressure.

Inline resistive heater 56 under control of control unit 100 is capable of heating fresh PD fluid to body temperature, e.g., 37° C., for delivery to patient P at a desired flowrate. Control unit 100 in an embodiment uses feedback from temperature sensor 58*a* in a PID temperature routine for pumping fresh PD fluid to patient P at a desired temperature. The control and operation of inline resistive heater 56 for heat disinfection is discussed in detail below.

FIG. 1 also illustrates that system 10 includes and uses a disposable filter set 40, which communicates fluidly with the fresh and used PD fluid lumens of dual lumen patient line 28. Disposable filter set 40 includes a disposable connector 42 that connects to a distal end 28*e* of reusable patient line 28. Disposable filter set 40 also includes a connector 44 that connects to the patient's transfer set. Disposable filter set 40 further includes a sterilizing grade filter membrane 46 that further filters fresh PD fluid. Disposable filter set 40 is provided in one embodiment as a last chance filter for PD machine 20, which has been heat disinfected between treatments. Any pathogens that may remain after disinfection, albeit unlikely, are filtered from the PD fluid via the sterilizing grade filter membrane 46 of disposable filter set 40.

FIG. 1 illustrates system 10 setup for treatment with PD fluid containers or bags 38*a* to 38*d* connected via reusable, flexible PD fluid lines 24*a* to 24*d*, respectively. Dual lumen patient line 28 is connected to patient P via disposable filter set 40. Disposable drain line 36 is connected to drain line connector 34. In FIG. 1, PD machine or cycler 20 of system 10 is configured to perform multiple patient drains, patient fills, patient dwells, and a priming procedure, as part of or in preparation for treatment.

Figure 2:
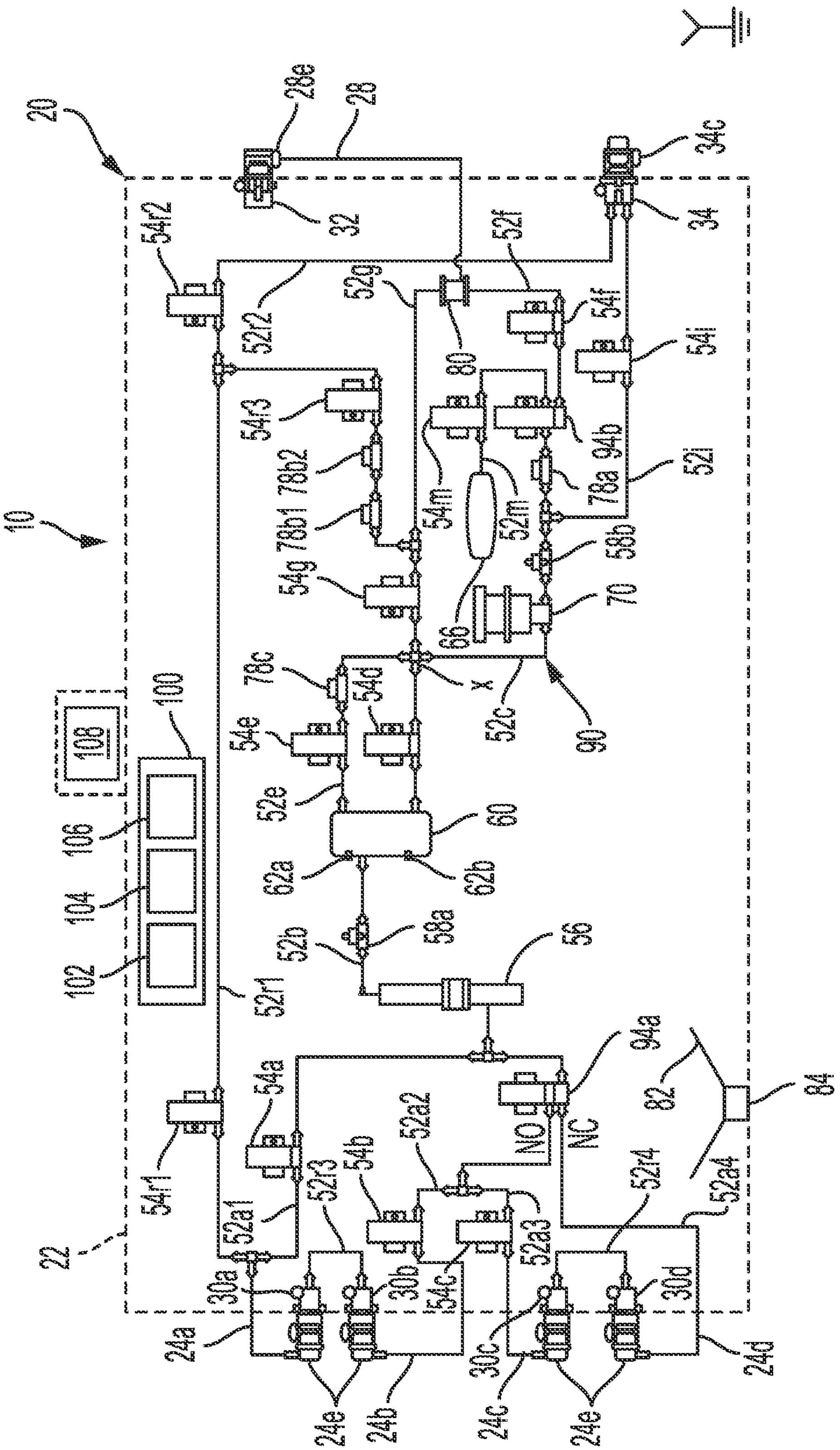
FIG. 2 is a fluid flow schematic of one embodiment for a medical fluid system, e.g., PD fluid system, that is set for disinfection.

FIG. 2 illustrates system 10 in a disinfection mode. PD fluid containers or bags 38*a* to 38*d* are removed and flexible PD fluid lines 24*a* to 24*d* are plugged instead in a sealed manner into disinfection or PD fluid line connectors 30*a* to 30*d*, respectively. Reusable dual lumen patient line 28 is disconnected from disposable filter set 40 (which is discarded), and distal end 28*e* of dual lumen patient line 28 is plugged sealingly into patient line connector 32. Disposable drain line 36 is removed from drain line connector 34 and discarded. Drain line connector 34 is capped via cap 34*c* to form a closed disinfection loop 90. PD machine or cycler 20 of system 10 in FIG. 2 is configured to perform a disinfection sequence, e.g., a heat disinfection sequence in which fresh PD fluid is heated via inline heater 56 to a disinfection temperature of, e.g., 75° C. or greater. PD fluid pump 70 circulates the heated PD fluid closed disinfection loop 90 for an amount of time needed to properly disinfect the fluid components and lines of the disinfection loop.

External Tubing Surface Disinfection

FIGS. 1 and 2 illustrate hose reel 80 for retracting dual lumen patient line 28 into housing 22 of PD machine 20 when desired. PD system 10 in one embodiment retracts reusable patient line 28 into housing 22 during disinfection, e.g., after treatment when patient P disconnects from filter set 40 and removes the filter set from the end of patient line 28. Internal hose reel 80 is in one embodiment spring-actuated to automatically pull dual lumen patient line 28 into housing 22 after treatment and before disinfection begins. Maintaining dual lumen patient line 28 within housing 22 during disinfection is advantageous because patient line 22 is held in a coiled arrangement such that there is less surface area to lose heat. Also, the coiled patient line 28 is retained within housing 22, which acts as a thermal insulator relative to ambient temperature and ambient air fluctuations. In short, retracting patient line 28 into housing 22 during heat disinfection increases the efficiency of same.

Figure 3:
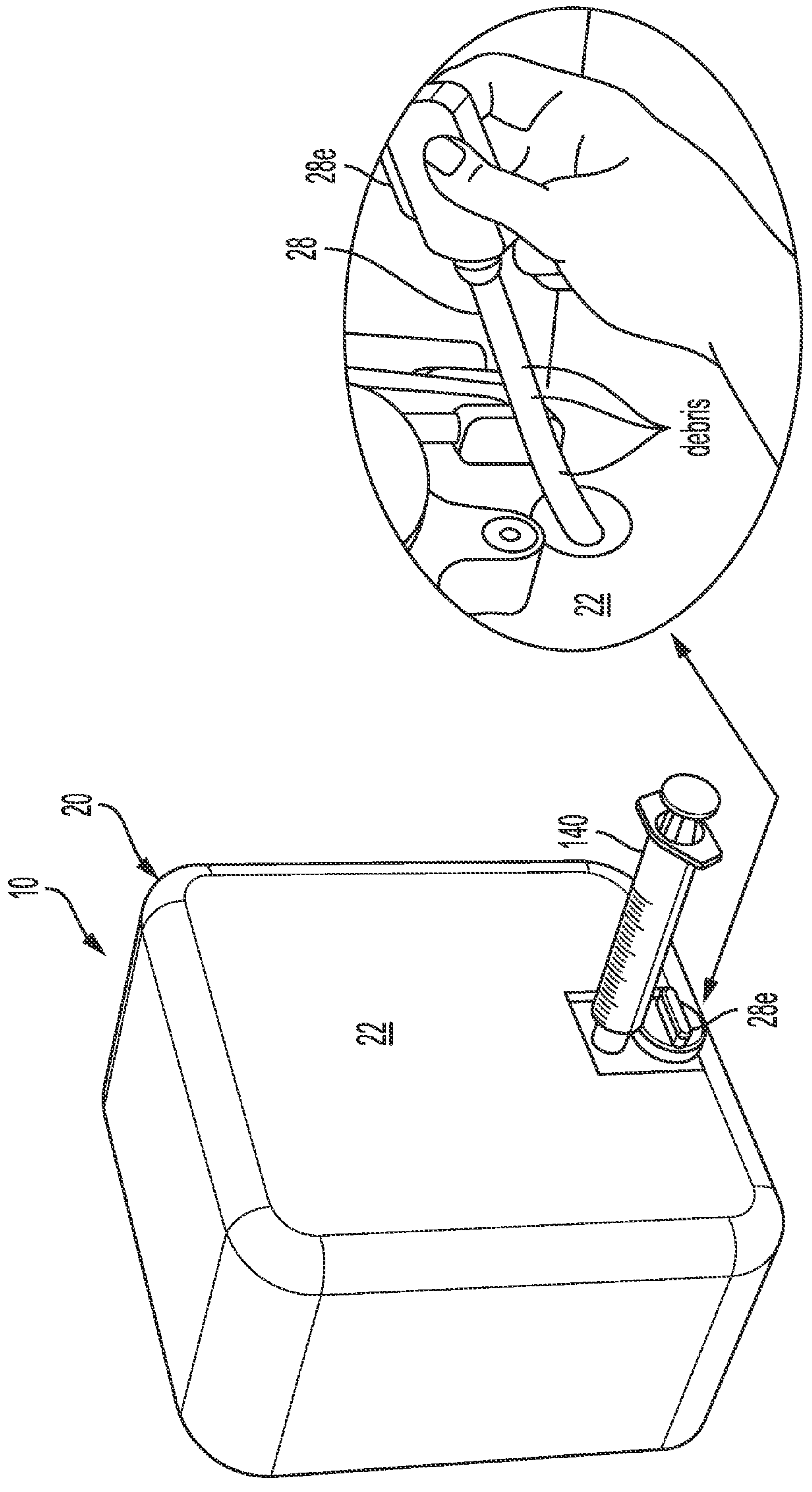
FIG. 3 is a perspective view illustrating one embodiment for a housing of a PD machine and a retractable and reusable PD fluid patient line of the present disclosure.

FIG. 3 illustrates that a problem associated with retracting dual lumen patient line 28 into housing 22 of PD machine 20 of system 10 is that debris collected by the patient line may be pulled into the housing. The debris may contaminate the internal components (see FIGS. 1 and 2) of PD machine 20 and possibly migrate into the inside of patient tubing 28. FIG. 3 further illustrates a syringe or other disinfectant administration device 140 for refilling disinfectant. As illustrated in FIGS. 4 to 9, PD machine 20 and associated system 10 and method of the present disclosure solves the debris collection problem by providing an external tubing surface cleaning unit 110 that removes debris from reusable tubing, such as dual lumen patient line 28, and applies a disinfectant to the tubing as the tubing is pulled into housing 22 of PD machine 20 via spring-actuated hose reel 80.

FIGS. 4 to 8 illustrate that external tubing surface cleaning unit 110 in one embodiment includes a collar 112. Collar 112 in the illustrated embodiment is formed from a first, e.g., upper, half 114 and a second, e.g., lower, half 116. First half 114 and second half 116 form an inner diameter 112*d* that has a shape that matches the shape of an outer diameter 28*d* of dual lumen patient line 28. Dual lumen patient line 28 may have a circular or substantially circular outer diameter in which case halves 114, 116 of collar 112 form a matching circular inner diameter 112*d*. Alternatively, dual lumen patient line 28 may have an oblong or elliptical outer diameter 28*d* in which case halves 114, 116 of collar 112 form a matching oblong or elliptical inner diameter 112*d*. Inner diameter 112*d* of collar 112 may be slightly larger than outer diameter 28*d* of dual lumen patient line 28.

FIGS. 4 to 8 also illustrate that a foam scrubber 120 is provided along the inner diameter of halves 114, 116 of collar 112, such that foam scrubber 120 extends around and contacts a full 360 degrees of dual lumen patient line 28 as the patient line is pulled through external tubing surface cleaning unit 110 of the present disclosure. Foam scrubber 120 in the illustrated embodiment has a cylindrical or tubular portion 122 that is held, e.g., mechanically press-fit and/or adhered, within halves 114, 116 of collar 112. Foam scrubber 120 also includes a disinfectant application extension 124 that extends from cylindrical or tubular portion 122 into a disinfectant reservoir 130.

Disinfectant reservoir 130 in the illustrated embodiment includes flat sides 132*a* to 132*d* and a rounded top 134. A bottom of disinfectant reservoir 130 in the illustrated embodiment is formed by first or upper half 114 of collar 112. Disinfectant reservoir 130 holds a disinfectant, such as an environmentally friendly disinfectant, e.g., citric acid or a povidone-iodine solution. Disinfectant application extension 124 of foam scrubber 120 allows the disinfectant to flow or migrate from disinfectant reservoir 130 to foam scrubber cylindrical or tubular portion 122, where the disinfectant may then be transferred to the exterior surface 28*d* of dual lumen patient line 28 as it is pulled through external tubing surface cleaning unit 110. Foam scrubber 120 accordingly wipes off the external surface or diameter 28*d* of patient line 28 and applies disinfectant to same.

Foam scrubber 120 may be made for example from polyurethane flexible foam or silicone foam, e.g., with a shore hardness ranging from Shore A50 to Shore A60, which has good absorption properties when dipped with disinfectant, for example, a povidone-iodine solution or citric acid. Collar 112 and disinfectant reservoir 130 are made of, e.g., molded from, one or more plastic in one embodiment, such as, polyvinylchloride ("PVC") or a non-PVC material, such as polyethylene ("PE"), polyurethane ("PU"), polycarbonate ("PC") and/or polyetheretherketone ("PEEK").

Figure 5:
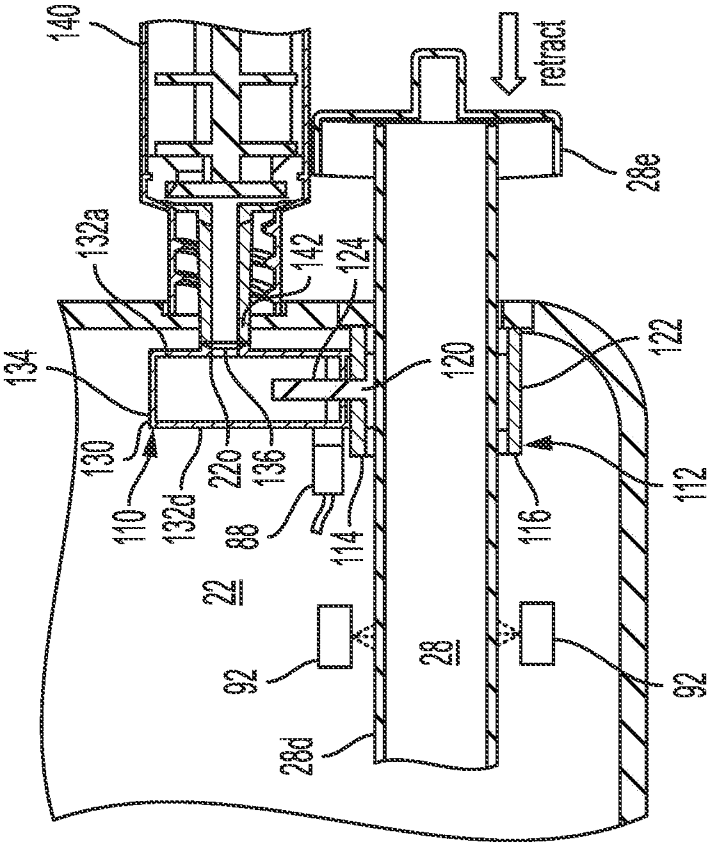
FIG. 5 is a side elevation view of one embodiment for an external tubing surface cleaning unit of the present disclosure shown mounted within the PD machine, wherein the reusable line, e.g., reusable patient line, is partially retracted within the PD machine.
Figure 4:
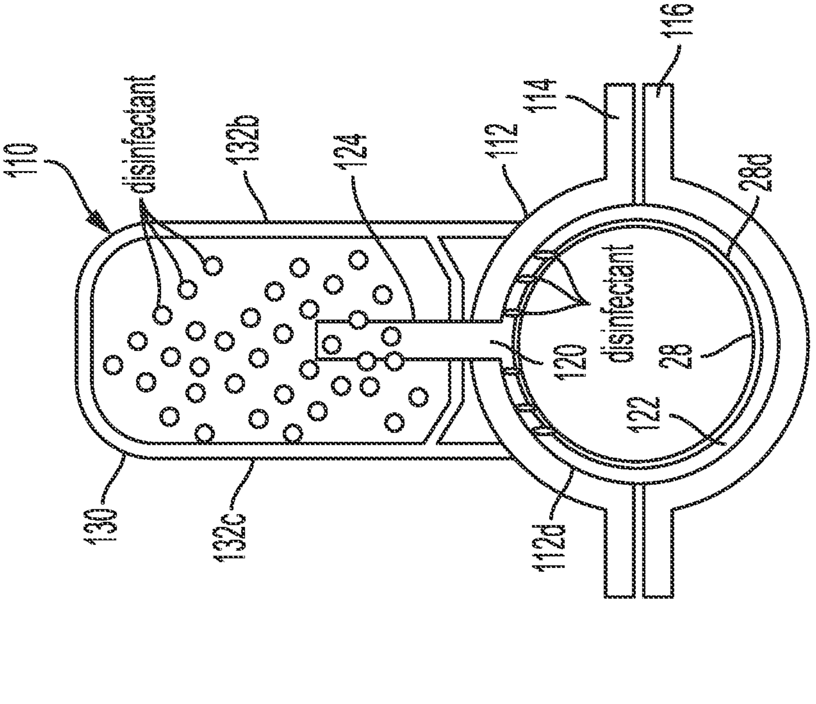
FIG. 4 is a front elevation view of one embodiment for an external tubing surface cleaning unit of the present disclosure.
Figure 6:
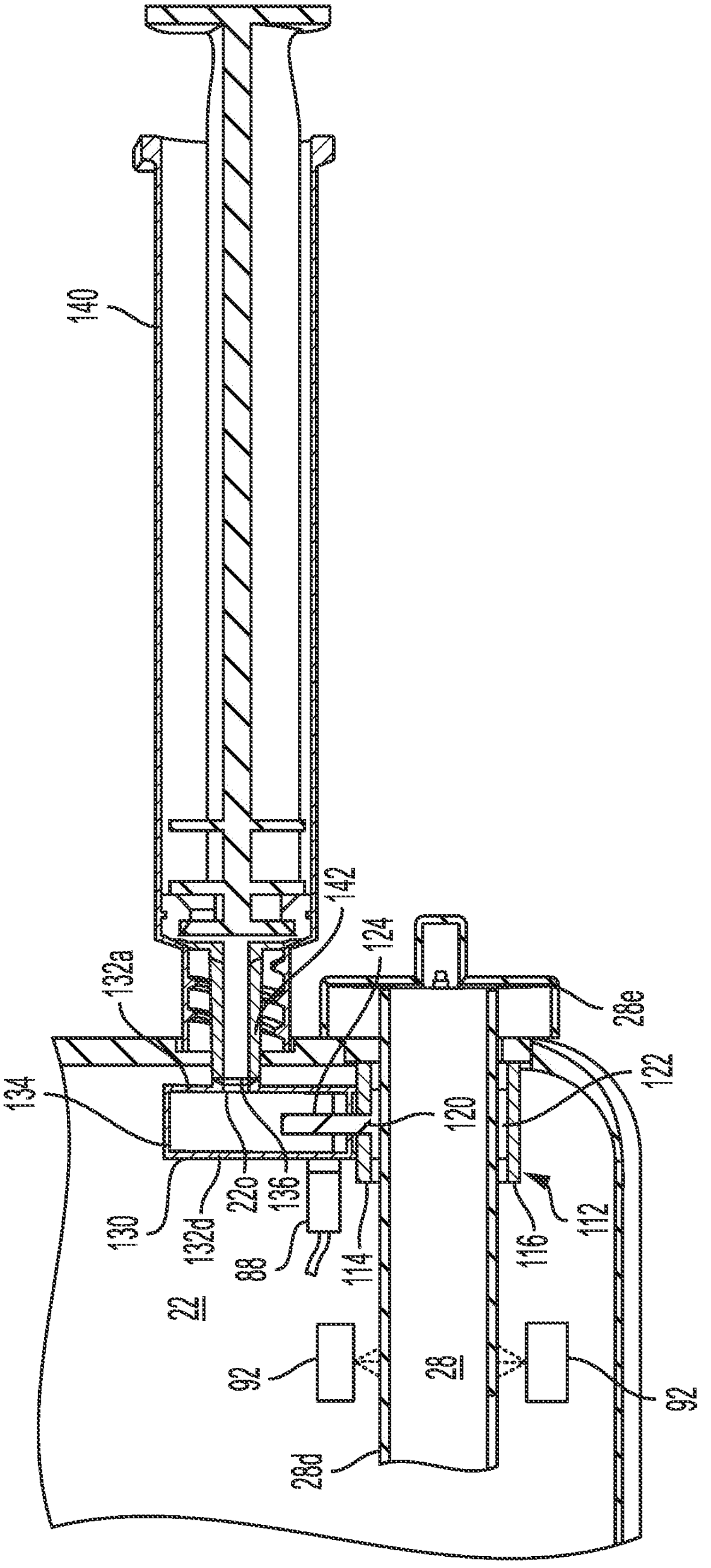
FIG. 6 is a side elevation view of one embodiment for an external tubing surface cleaning unit of the present disclosure shown mounted within the PD machine, wherein the reusable line, e.g., reusable patient line, is fully retracted within the PD machine.
Figure 7:
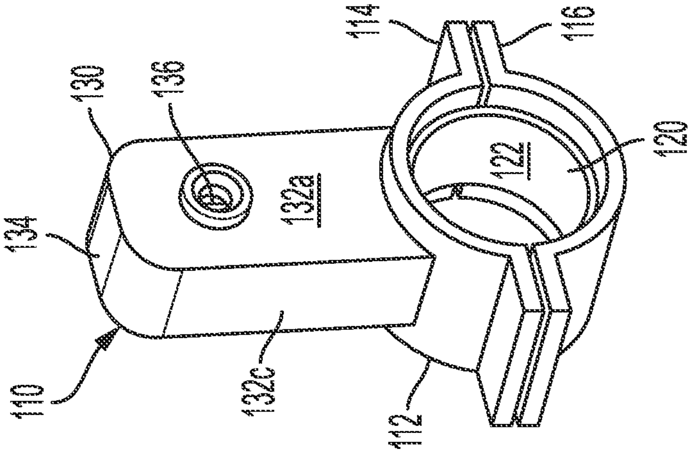
FIG. 7 is a front perspective view of an attachable, detachable and replaceable external tubing surface cleaning unit of the present disclosure.

FIGS. 5 to 7 illustrate that in one embodiment, flat side 132*a* of reservoir 130 includes a sealed septum or other type of openable sealed closure 136 that accepts the tip 142 (FIGS. 5, 6) of a syringe 140 or other type of disinfectant administration device. The patient or caregiver periodically fills the syringe or other disinfectant administration device 140 with disinfectant, e.g., citric acid or a povidone-iodine solution. The patient then inserts distal tip 142 of disinfectant administration device 140 through the openable sealed closure 136 and causes disinfectant to be distributed from disinfectant administration device 140 into disinfectant reservoir 130 to fill the reservoir with disinfectant, e.g., citric acid or a povidone-iodine solution. Once the filling of reservoir 130 is complete, the user or caregiver removes disinfectant administration device 140 from reservoir 130, after which the openable sealed closure 136 either self-seals closed or is sealed closed via the patient or caregiver, e.g., applying a threaded cap.

Knowing when to refill disinfectant reservoir 130 may be accomplished in a plurality of ways. In one embodiment, the disinfectant level is visible to the user, wherein at least one side 132*a* to 132*d* of reservoir 130 is made of a clear or non-opaque material such that the patient or caregiver is able to visually discern when to add disinfectant to the reservoir. Alternatively or additionally, one or more low level sensor 88 outputting to control unit 100 is provided with PD machine 20. Low level sensor 88 as illustrated in FIGS. 5 and 6 is positioned and arranged adjacent to disinfectant reservoir 130 so as to be able to detect when the level of disinfectant has fallen below a refill level, indicating that the reservoir needs to be refilled. One or more level sensor 88 sends a corresponding signal to control unit 100 that is indicative of the low disinfectant level, upon which control unit 100 cause user interface 108 to provide an audio, visual or audiovisual message to the patient or caregiver instructing that the disinfectant reservoir needs to be refilled. User interface 108 may also provide a refill confirm button or selector that the patient or caregiver needs to press after refilling the disinfectant, e.g., in order for a next treatment to be performed. One or more low level sensor 88 may, for example, be a Hall effect, magnetic, inductive, capacitive or optical sensor.

Alternatively or additionally, control unit 100 may cooperate with the patient or caregiver to know when to refill reservoir 130 with disinfectant. In one embodiment, the patient upon refilling disinfectant reservoir 130 presses or enters a refill confirm button or input into user interface 108 of control unit 100. Control unit 100 at that point knows that reservoir 130 is full. Control unit 100 is also programmed to know how much disinfectant is used for each retraction of dual lumen patient line 28, i.e., how many disinfection sequence patient line retractions may be performed after disinfectant reservoir 130 is refilled. When control unit 100 determines that the current retraction is at or near the refill limit, control unit 28 causes user interface 10 to provide an audio, visual or audiovisual message to the patient or caregiver instructing that the disinfectant reservoir needs to be refilled.

FIGS. 5 and 6 further illustrate that in one embodiment, one or more ultraviolet ("UV") light 92 is provided to disinfect the outside of dual lumen patient line 28 in addition to the disinfection provided by the liquid disinfectant. In an embodiment, control unit 100 energizes UV light 92 automatically upon a sensor (not illustrated), such as a proximity, optical or magnetic sensor, sensing the rotation of hose reel 80, and indicating same to the control unit. Here, UV light 92 is energized automatically while reusable patient line 28 is retracted into housing 22 of PD machine 20. UV light kills pathogens located on the outside of reusable patient line 28. It may thus be possible to keep scrubber 120 of cleaning unit 110 for the purpose of wiping off the outside of reusable patient line 28, while removing the liquid disinfectant from the cleaning unit and instead relying on UV light disinfection.

External tubing surface cleaning unit 110 of the present disclosure may be implemented in a plurality of different ways. In a first way as illustrated in FIGS. 3, 5 and 6, cleaning unit 110 is provided primarily as an integrated and largely durable or reusable unit. Collar 112 and reservoir are permanent unless damaged and needing replacement, while foam scrubber 120 may be a semi-permanent component that is replaced periodically. The patient is provided with reusable syringe or other disinfectant administration device 140 and a supply of disinfectant (not illustrated), such as bag or jug of citric acid or povidone-iodine solution, which is replaced periodically.

As illustrated in FIGS. 3, 5 and 6, external tubing surface cleaning unit 110 in the integrated embodiment is located within housing 22 of PD machine 20, such that it is largely hidden from the patient or caregiver. Cleaning unit 110 may for example be bolted to and/or snap-fitted to the inside of housing 22. As illustrated in FIGS. 5 and 6, housing 22 provides an opening 22*o*, such that septum or other type of openable sealed closure 136 provided at side 132*a* of reservoir 132 is visible and accessible from the outside of housing 22, such that the reservoir may be accessed by the patient or caregiver for disinfectant refill.

Figure 8:
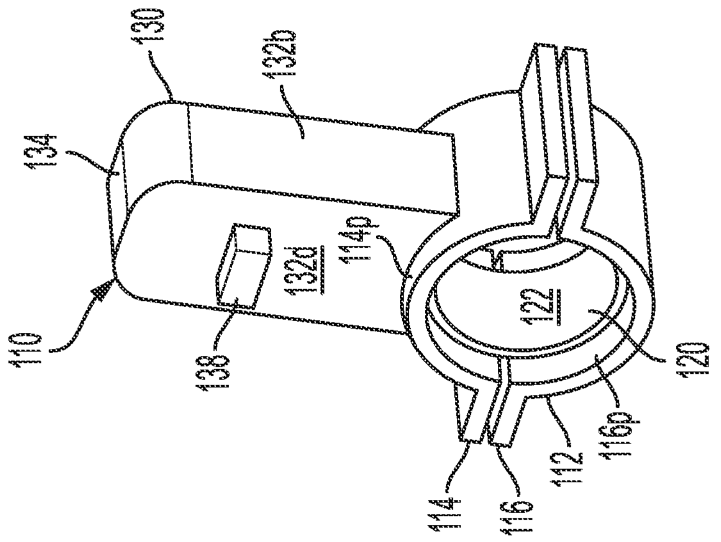
FIG. 8 is a rear perspective view of an attachable, detachable and replaceable external tubing surface cleaning unit of the present disclosure.
Figure 9:
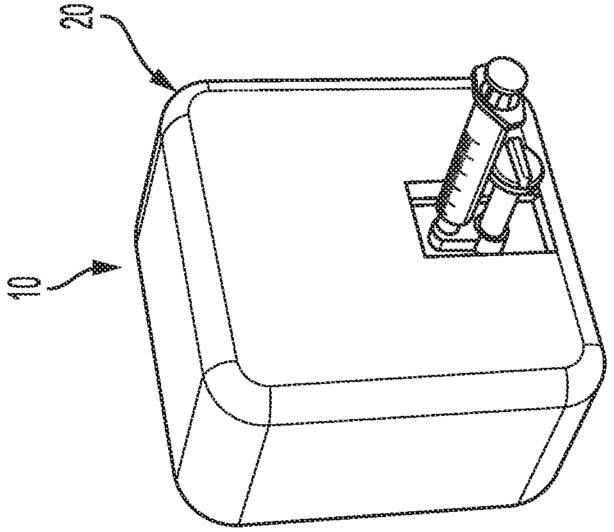
FIG. 9 is a front perspective view of an attachable, detachable and replaceable external tubing surface cleaning unit of the present disclosure abutted against a PD machine for operation.

As illustrated in FIGS. 7 to 9, in a second way, external tubing cleaning unit 110 is provided as an attachable, detachable and replaceable unit. Here, collar 112, disinfectant reservoir 130 and foam scrubber 120 may be semi-permanent components, wherein external tubing cleaning unit 110 is removed and replaced as a whole when needed, e.g., when foam scrubber 120 needs replacement. Septum or other type of openable sealed closure 136 may again be provided at side 132*a* of disinfectant reservoir 130 so that the patient or caregiver can introduce new disinfectant when needed. The patient may again be provided with a reusable syringe or other disinfectant administration device 140 and a supply of disinfectant (not illustrated), such as citric acid or a povidone-iodine solution, which is replaced periodically. In an alternative embodiment, openable sealed closure 136 is not provided and external tubing cleaning unit 110 is instead replaced when disinfectant reservoir 130 runs out of disinfectant.

As illustrated in FIG. 8, any version of detachable and replaceable cleaning unit 110 may include a tab or other feature 138 provided at reservoir 130, e.g., at flat side 132*d* of the reservoir. Tab or other feature 138 is sized and shaped to snap-fit into a mating aperture (not illustrated) formed in housing 22 of the PD machine. FIG. 8 also illustrates that portions 114*p*, 116*p* of halves 114, 116 of collar 112 may also be used to snap-fit into a mating aperture (not illustrated) formed in housing 22 of PD machine 20. Providing multiple snap-fitting engagements (e.g., via tab or other feature 138 and collar portions 114*p*, 116*p*) helps external tubing cleaning unit 110 to remain stable as the reusable line, e.g., reusable dual lumen patient line 28 is pulled through cleaning unit 110 while being scrubbed and disinfected via contact with foam scrubber 120.

Alternative Embodiments

In various alternative embodiments, while system 10 is described above with pulling reusable patient line 28 through external tubing cleaning unit 110 automatically via spring-actuated hose reel 80, a spring-actuated hose reel 80 is not required. Instead, a hose reel that is manually operated, e.g., via a rotating handle located outside of housing 22, may be provided instead. Here, reusable patient line 28 is pulled through external tubing cleaning unit 110 manually. Control unit 100 may cause user interface 108 to prompt the patient or caregiver to manually retract reusable patient line 28 into housing 22 after treatment and prior to disinfection.

Further alternatively, while housing 22 of PD machine 20 is illustrated as providing an opening 22*o*, such that the user may access openable sealed closure 136 of reservoir 130 for disinfectant refill, reservoir 130 is instead refilled from a disinfectant source, e.g., citric acid container or bag 66 (used also during disinfection) located within housing 22 as illustrated in FIGS. 1 and 2. Here, a tube (not illustrated) such as a flexible plastic tube may run from disinfectant container or bag 66 to the top of reservoir 130. Disinfectant container or bag 66 may be located elevationally above reservoir 130 such that the disinfectant gravity flows into reservoir 130. The head pressure of disinfectant container or bag 66 may also drive disinfectant into reservoir 130. A sensor, such as any type described herein for low level sensor 88, may be provided as a low level sensor at disinfectant container or bag 66, which outputs to control unit 100. Control unit 100 accordingly knows when the disinfectant within container or bag 66 is low and causes user interface 108 to audibly, visually or audiovisually prompt the patient or caregiver to install a new disinfectant container or bag 66.

In a further alternative embodiment, reservoir 130 is not filled with disinfectant and instead the tube (not illustrated) from container or bag 66 extends into reservoir 130 and terminates just above scrubber 120 so as to be able to dispense disinfectant onto scrubber 120, e.g., just prior to the retraction of reusable patient line 28 through the scrubber. Here, a valve (not illustrated) may be provided along the tube. Control unit 100 causes the valve to open, e.g., after treatment and prior to the patient line retraction, wherein the valve remains open for only a period of time enough for tubular portion 122 of scrubber 120 to become fully wetted or saturated with disinfectant. If it is determined to be needed, control unit 100 may also open the valve during the retraction of reusable patient line 28 through scrubber 120.

In yet another alternative embodiment, the valve just described is replaced with a clamp. The clamp is in one embodiment normally spring-biased closed. A lever is provided, which actuates the spring (compresses or stretches the spring), allowing the tube extending from disinfectant container or bag 66 or bag to open so that the disinfectant is dispensed onto scrubber. The lever is actuated via a button provided at housing 22 of PD machine 20. When the user releases the button, the spring pushes the button back to its normal unactuated position and causes the clamp to occlude the tube extending from disinfectant container or bag 66, shutting off the flow of the disinfectant. Control unit 100 is in one embodiment programmed to cause user interface 108 to audibly, visually or audiovisually prompt the patient or caregiver to press the button before and/or during retraction of reusable patient line 28.

In yet a further alternative embodiment, the external tubing cleaning unit 110 is located on the outside of housing 22 of PD machine 20 where it is easy to load disinfectant into reservoir 130. Tubular portion 122 of foam scrubber is 120 provided as two halves, one each connected to first half 114 and second half 116 of collar 112. The collar and scrubber halves are normally spring-biased to not contact reusable patient line 28. One or more button is provided to allow the patient or caregiver to force the halves of foam scrubber 120 against the spring-bias and into contact with reusable patient line 28 as it is being retracted into housing 22. When the patient releases the one or more button, the one or more spring is released so as to bias the halves of foam scrubber 120 away from reusable patient line 28. Control unit 100 is in one embodiment programmed to cause user interface 108 to audibly, visually or audiovisually prompt the patient or caregiver to press or otherwise actuate the one or more button before and/or during retraction of reusable patient line 28.

In still a further alternative embodiment, external tubing cleaning unit 110 is provided as a separate handheld unit, which is again configured for easy disinfectant loading. Here, the handheld tubing cleaning unit 110 may be provided as a clamshell with reservoir 130 provided in hinged halves which are each filled with disinfectant. Foam scrubber 120 is also provided in halves, one each for the halves of reservoir 130. Where each half of scrubber 120 is attached to a half of reservoir 130, the reservoir is provided with holes or perforations for allowing the liquid disinfectant to fully wet or saturate the foam scrubber material. Control unit 100 in an embodiment causes user interface 108 to audibly, visually or audiovisually prompt the patient or caregiver to place handheld external tubing cleaning unit 110 around reusable patient line 28, directly adjacent to housing 22, as the patient or caregiver initiates the spring-actuated retraction of the patient line via hose reel 80.

It should be understood that other various changes and modifications to the presently preferred embodiments described herein will be apparent to those skilled in the art. It is therefore intended that such changes and modifications be covered by the appended claims. For example, while system 10 is described as cleaning and disinfecting the external surface of dual lumen patient line 28, system 10 may clean and disinfect the external surface of any tube that is retracted into housing 22 of PD machine 20. For example, system 10 may clean and disinfect the external surface of any one or more of reusable PD fluid lines 24*a* to 24*d* if pulled into housing 22. System 10 may clean and disinfect the external surface of drain line 36 if instead made to be reusable and pulled into housing 22. Also, while scrubber 120 is described as being a foam scrubber, scrubber 120 could alternatively be made of a fabric or fibrous material that allows disinfectant to flow through the scrubber.

The invention is claimed as follows:

1. A peritoneal dialysis ("PD") system comprising:
a housing;
a PD fluid pump housed by the housing;
a reusable PD fluid line in fluid communication with the PD fluid pump, the reusable PD fluid line positioned and arranged to be pulled into the housing; and
an external tubing surface cleaning unit configured and positioned to at least one of (i) remove debris from at least a portion of an exterior of the reusable PD fluid line as it is pulled into the housing, or (ii) apply disinfectant to at least the portion of the exterior of the reusable PD fluid line as it is pulled into the housing,
wherein the external tubing surface cleaning unit includes a scrubber sized and shaped to extend around and contact the reusable PD fluid line to remove debris from at least the portion of the exterior of the reusable PD fluid line as it is pulled into the housing.

2. The PD system of claim 1, wherein the reusable PD fluid line is a reusable patient line.

3. The PD system of claim 2, wherein the reusable patient line is a reusable dual lumen patient line.

4. The PD system of claim 1, which includes a hose reel located within the housing, the hose reel configured to pull the reusable PD fluid line into the housing.

5. The PD system of claim 1, which includes a control unit configured to cause a disinfection sequence to be performed in which an interior of the reusable PD fluid line is disinfected, and wherein the reusable PD fluid line is pulled into the housing prior to the disinfection sequence being performed.

6. The PD system of claim 1, wherein the scrubber is a foam or fibrous scrubber formed so as to apply the disinfectant to at least the portion of the exterior of the reusable PD fluid line as it is pulled into the housing.

7. The PD system of claim 6, wherein the foam or fibrous scrubber includes a cylindrical portion sized and shaped to extend around and apply the disinfectant to the reusable PD fluid line, and a disinfectant application extension extending from the cylindrical portion into a disinfectant reservoir, wherein the disinfectant application extension allows the disinfectant from the disinfectant reservoir to flow to the cylindrical portion.

8. The PD system of claim 7, wherein the cylindrical portion of the foam or fibrous scrubber is supported by a collar, the disinfectant reservoir extending from the collar.

9. The PD system of claim 1, wherein the external tubing surface cleaning unit includes a disinfectant reservoir configured to hold the disinfectant for application to at least the portion of the exterior of the reusable PD fluid line as it is pulled into the housing.

10. The PD system of claim 9, wherein the disinfectant reservoir includes an openable sealed closure configured to allow the disinfectant to be introduced into the disinfectant reservoir.

11. The PD system of claim 10, which includes a disinfectant administration device, wherein the openable sealed closure is configured to receive a tip of the disinfectant administration device such that the disinfectant administration device is able to introduce the disinfectant into the disinfectant reservoir.

12. The PD system of claim 9, which includes a source of disinfectant and a tube leading from the source of disinfectant to the disinfectant reservoir.

13. A peritoneal dialysis ("PD") system comprising:
a housing;
a PD fluid pump housed by the housing;
a reusable PD fluid line in fluid communication with the PD fluid pump, the reusable PD fluid line positioned and arranged to be pulled into the housing; and
an external tubing surface cleaning unit located within the housing and configured and positioned to at least one of (i) remove debris from at least a portion of an exterior of the reusable PD fluid line as it is pulled into the housing, or (ii) apply disinfectant to at least the portion of the exterior of the reusable PD fluid line as it is pulled into the housing,
wherein the housing provides an opening allowing an openable sealed closure of the external tubing surface cleaning unit to be accessed for refilling disinfectant.

14. A peritoneal dialysis ("PD") system comprising:
a housing;
a PD fluid pump housed by the housing;
a reusable PD fluid line in fluid communication with the PD fluid pump, the reusable PD fluid line positioned and arranged to be pulled into the housing; and
an external tubing surface cleaning unit attachable to and detachable from the housing and configured and positioned to at least one of (i) remove debris from at least a portion of an exterior of the reusable PD fluid line as it is pulled into the housing, or (ii) apply disinfectant to at least the portion of the exterior of the reusable PD fluid line as it is pulled into the housing,
wherein the housing defines at least one mating aperture, and wherein the external tubing surface cleaning unit includes at least one feature sized and shaped to snap-fit within the at least one mating aperture.

15. A peritoneal dialysis ("PD") system comprising:
a housing;
a PD fluid pump housed by the housing;
a reusable PD fluid line in fluid communication with the PD fluid pump, the reusable PD fluid line positioned and arranged to be pulled into the housing; and
an external tubing surface cleaning unit configured and positioned to at least one of (i) remove debris from at least a portion of an exterior of the reusable PD fluid line as it is pulled into the housing, or (ii) apply disinfectant to at least the portion of the exterior of the reusable PD fluid line as it is pulled into the housing,
wherein the external tubing surface cleaning unit includes a disinfectant reservoir, and wherein the system includes at least one sensor positioned and arranged to detect a level of disinfectant within the disinfectant reservoir.

16. The PD system of claim 15, which includes a control unit and a user interface, the at least one sensor outputting to the control unit, and wherein the control unit is configured to cause the user interface to prompt for a disinfectant refill when an output from the at least one sensor indicates a low disinfectant level within the disinfectant reservoir.

17. A peritoneal dialysis ("PD") system comprising:
a PD machine including a housing;
a reusable PD fluid line positioned and arranged to be pulled into the housing; and
an external tubing surface cleaning unit configured and positioned to disinfect at least a portion of an exterior of the reusable PD fluid line as it is pulled into the housing using at least one ultraviolet ("UV") light.

18. A peritoneal dialysis ("PD") method comprising:
enabling a reusable PD fluid line to be retracted into a PD fluid machine; and causing disinfectant to be applied to at least a portion of an exterior of the reusable PD fluid line as it is retracted into a housing using an external tubing surface cleaning unit, the disinfectant being provided from a source of disinfectant and a tube leading from the source of disinfectant into the external tubing surface cleaning unit.

* * * * *